United States Patent [19]

Thorell

[11] 4,158,135

[45] Jun. 12, 1979

[54] ANALYSIS PROCESS

[76] Inventor: Jan I. Thorell, Beleshögsvägen 1, S-216 18 Malmö 1, Sweden

[21] Appl. No.: 821,108

[22] Filed: Aug. 2, 1977

[30] Foreign Application Priority Data

Aug. 16, 1976 [SE] Sweden ............................... 7609120

[51] Int. Cl.² .................... G01T 1/161; G01T 1/20
[52] U.S. Cl. ................................. 250/303; 250/364; 250/432 R
[58] Field of Search .............. 250/302, 304, 303, 328, 250/364

[56] References Cited

U.S. PATENT DOCUMENTS

| | | | |
|---|---|---|---|
| 3,451,777 | 6/1969 | Giulio | 250/303 |
| 3,615,222 | 10/1971 | Mead | 250/303 |
| 3,883,738 | 5/1975 | Glover et al. | 250/304 |

Primary Examiner—Harold A. Dixon
Attorney, Agent, or Firm—Fred Philpitt

[57] ABSTRACT

A method of analysis in which a radioactive substance is distributed in a liquid phase and a solid particle phase and radiation from one phase is measured while attenuating the radiation from the other phase, the radiation from said other phase being shielded according to the invention by virtue of the fact that said phase is mixed with and/or contains a radiation-absorbing material in such a quantity and concentration that the dominant portion of the radiation from this phase will be absorbed.

10 Claims, No Drawings

ANALYSIS PROCESS

The present invention relates to a method for analysis of radioactivity in systems where a radioactive substance is distributed into a liquid phase and a solid, particulate phase, and in which radiation from one phase is measured whilst shielding the radiation from the other phase. Such methods makes it possible to measure the radiation from one of the phases of this system as well as its distribution between the phases without the removal of the other phase.

Such a method is known from Swedish Patent Application No. 7201643-4. In this known method, shielding is effected either by designing the tube, in which the two phases are located, in a particular manner, for example by giving the tube the form of a centrifuge tube with a thin capillary projecting out from the bottom of the tube assuming that the solid phase would be housed in the capillary. This known method also involves a precise and careful collimation of the detector. In this latter case, there may be used, for example, a partially shielded holder with a lead base which shields the solid phase when the holder, with the tube containing the liquid phase and the solid phase inserted therein, is placed in an instrument for measuring the radioactivity of the liquid phase, or alternatively two lead-shields can be used, these shields being incorporated in the instrument for measuring the radioactivity and, in addition to shielding one of the phases, also shielding parts of the other phase in a manner such that the radioactivity of only part of the first phase is measured.

Embodiments which require the use of this specially designed centrifuge tube exclude the use of the conventional, simple centrifuge tubes.

When such specially designed tubes having a capillary on the underside of the tube are used, the solid phase is liable to settle in the capillary during the incubation stage, in which stage radioactivity is distributed between the solid and the liquid phase, thereby rendering it impossible for the settled, solid phase to react with the radioactive material contained in the soluble phase. Even though the specially designed tube is rotated during the incubation stage, there remains the risk that part of the incubate will be drawn into the capillary tube by the capillary forces and in this way be omitted from the reaction. Further, there is nothing to prevent liquid from passing down into the capillary. The wider the capillary the more liquid that will pass down thereinto. The narrower the capillary the more difficult it becomes to force the particles thereinto. Finally, the reproduceability of this embodiment is not satisfactory.

In the case of embodiments in which precise and careful collimation of the detector is effected lead shields must be placed externally of the centrifuge tube, which prevents the use of conventional well type of detector for measuring the gamma radiation. This method therefore requires construction of a special type of detector or modification of available detectors. Moreover, because of the necessary complexity of the shielding arrangement, high measurement losses are experienced and each measuring operation must be carried out in exactly the same manner as a preceding operation.

As a result, the aforementioned method has not been used in practice and still, the conventional technique is the one generally applied, in which the phases are physically separated from one another after which the radioactivity of one of the isolated phases is measured.

In accordance with the present invention there is now proposed an improved method of the type mentioned in the introduction. This new method avoids the difficulties mentioned above. Conventional centrifuge tubes can be used and measurement losses reduced considerably in comparison with the known methods. The method can be used in any counting instrument without modification of the detector.

The method according to the invention is characterised by the fact that radiation from the second phase is shielded by virtue of the fact that said phase is mixed with or contains a radiation-absorbing material in such a quantity and concentration that the dominating portion of the radiation from this phase would be absorbed. Accordingly, only the radiation from the other phase will emerge out of the sample despite the fact that both phases are present. When using the radioactive isotope Iodine-125 which is the one most used in the present context, whose gamma radiation has an energy band of 27–35 keV, an effective attenuation of the radiation may be achieved with a wide variety of elements, even those with a relatively low Z-number. In addition to the Z-number, the absorption effect also depends upon the energy contained by the electrons, i.e. electrons occupying the so-called K- and L-shells. For this reason many elements like silver, cadmium, tungsten, and bismuth are very effective in absorbing radiation from Iodine-125. Thus, if the radioactivity is uniformly distributed in a sphere having a volume of 200 $\mu$l, it can be ascertained that only a 5% content of cadmium is required to absorb 90% of the radiation emitted.

In accordance with one embodiment of the method according to the invention, the radiation-absorbing material is in particle form and is insoluble in the liquid phase, and is applied to the solid phase prior to or whilst or after separating (e.g. by centrifugation) the solid phase from the liquid phase.

According to a preferred embodiment of the method according to the invention, the radiation-absorbing material is in particle form and is insoluble in the liquid phase and part of said material is added to the solid phase prior to and/or whilst separating (e.g. by centrifugation) the solid phase from the liquid phase, while the residue of said radiation-absorbing material is added subsequent to said separation.

According to a further embodiment, the liquid phase is shielded by using as the radiation-absorbing material a substance which is soluble in the liquid phase. In this case the substance may, for example, be an inorganic or an organic iodo-compound, such as sodium iodide, soluble in the liquid phase. This substance is added in the form of a solution or as a substance which dissolves in the liquid phase. In an alternative embodiment, the radiation-absorbing material is in a liquid form, but which is immiscible with liquid phase containing the radioactive material.

The phases are normally separated so that the solid phase lies beneath the liquid phase. It is possible, in principle, however, to select the densities of the two phases so that the liquid phase lies beneath the solid phase. In both cases it may be suitable, in certain instances, to place between the two phases a further one or more non-radioactive phases, so as to separate the two first mentioned phases one from each other. To this end there can be used a liquid having a density which lies between the densities of the two first mentioned phases and which is immiscible with the liquid in the radioactive liquid phase and in which neither the solid phase nor the radioactive substance dissolved in the liquid phase can dissolve. Such an intermediate phase (solid or liquid) may also be used when the solid phase has a greater density than the liquid phase.

According to the present invention, contact between the radioactive liquid and the radioactive particles may or may not be broken by one or more layers of non-radioactive substances, these layers having a greater or lesser thickness and the substances being in the form of radiation-absorbing particles and/or non-radiating liquid, when the solid phase is shielded and/or a second liquid phase is brought between the first liquid phase and the solid phase. This enables measurements to be made with a high degree of accuracy.

The radiation-absorbing material may advantageously be an element having a Z-number higher than 25, preferably higher than 31, for example higher than 34, in its basic form or in the form of a chemical compound containing the element. Preferably, the material is in particle form, although other forms may be used, such as for example solutions which are immiscible with the liquid phase in the sample to be analysed. When the radiation-absorbing material is in particle form, particles of different density and/or size may be used simultaneously. By using a suitable particle size distribution, only one centrifugation step is needed to cause the radiation-absorbing substance to cover the solid phase both above and below. A radiation-absorbing material of higher density than both the solid and the liquid radioactive phases may be used to underlayer both of them, which predominantly would absorb the radiation directed downwards. Various combinations of attenuating material with different densities or particle sizes make it possible to achieve an optimal distribution of the radioactive phase to be attenuated within the attenuator. In the case of a radiation-absorbing material in liquid form, its density may be selected so as to achieve an optimal mixing with the phase from which the radiation is absorbed. It is also possible for the same purpose to utilize combinations of particulate and liquid radiation-absorbing media or combinations of different immiscible liquid absorber with different densities. Examples of radiation-absorbing substances which can be used in the method according to the invention include lead dioxide, cadmium carbonate, barium sulphate, metallic powders of silver, tungsten and cadmium, and insoluble iodo and bismuth compounds. The types and the quantities of radiation-absorbing substances used depends upon the radionuclide whose radiation is to be blocked. The dominating radionuclide within radioimmunisation analyses as $^{125}I$, whose radiation has a very low penetrating effect and therefore enables a selection to be made between a large number of radiation-absorbing substances.

The method according to the invention can, in principle, be used with any analysis in which a radioactive substance or compound is separated into a liquid phase and a solid particle phase. A common analysis of thio type in which an unknown quantity of a certain substance in a sample competes with a standard quantity of a radioactively labelled form of said substance in a reaction with a standard quantity of another substance. In these methods, called radioligand methods, the important parameter to be measured is the amount of the radioactive substance that has reacted. This is measured by quantitation of alternatively the reacted or the unreacted radioactivity, after either of these forms has been transferred into an insoluble form. To achieve this insolubilisation different methods can be used, such as those methods comprising double antibody separation, chemical precipitation or by utilizing antibodies or antigens bound to water-insoluble polymers in particle form.

In the latter case it is possible, for example, for (a) the polymer-bound antibody to react with antigens in the sample and with labelled antigens or (b) the polymer-bound antibody to react with the antigen in the sample so that the antigen is bound to the polymer-bound antibody, whereafter a labelled antibody is added which attaches itself to the bound antigen, or (c) the polymer-bound antigen is reacted with antibodies in the sample in a manner such that the antibody attaches itself to the antigen, whereafter labelled antigen is added this antigen attaching itself to the bound antibody, or (d) the polymer-bound antigen is reacted with antibodies in the sample in a manner such that the antibody attaches itself to the antigen, whereafter labelled antibodies are added, which antibodies are directed to the first-mentioned antibodies and attach themselves thereto. The polymer-bound antibodies may also be bound across antigens to the polymer and the polymer-bound antigens may also be bound across antibodies to the polymer.

These methods are found more clearly described in the literature, see for example "Radioimmunoassay methods" (editors: K. E. Kirkham and W. M. Hunter, Churchill Livingstone, London 1971). In another widely used method the unreacted radioactive material is rendered insoluble by adsorbing it to a particulate adsorber, usually active charcoal. The method according to the invention can be used for this modification, either by mixing the charcoal with a radiation absorbing material in analogy with the embodiments given above. An alternative embodiment combines these two effects in one by utilizing a radioactive absorber which also adsorbs the unreacted radioactive material. An example of a material with this property is bismuth carbonate powder. In analogy with this embodiment the radiation absorber may bind or otherwise combine with any of the radioactive material thereby both transferring it to a non-soluble form and absorbs its radiation.

The invention will now be described in more detail with reference to a number of examples. It will be seen that the results of the analyses coincide well with the complicated and laborious, although accurate technique now generally used and in which the phases are physically separated from one another.

EXAMPLE 1

This example illustrates the use of the invention with a radioimmuno-assay method whilst using antibodies coupled to a solid phase (cf. Biochim. Biophys. Acta 130 (1966), pages 257–260 and Scand. J. Clin. Lab. Invest. 31 (1973), pages 187–190).

0.1 ml of a buffer solution containing a constant quantity of radioactive $^{125}I$-insulin was pipetted to a series of test tubes (11×55 mm of polystyrene). 0.1 ml of a buffer solution containing specific quantities of insulin (standard solution) was then added. The quantities of insulin used were 0, 40 and 200 microunits ($\mu U$), and respective concentrations were added in triplicate (i.e. three tubes with 0, three tubes with 40, and three tubes with 200 $\mu U$).

Finally, to each tube was added 1 ml of a buffer solution containing a constant quantity of insulin antibodies coupled in covalent mode to particles of cross-linked dextran (from Pharmacia Diagnostics AB, Sweden), 1 ml of a buffer solution was added to a separate tube instead of the solution containing particles of the cross-linked dextran, for measuring the total quantity of radioactivity present in each test tube. The tubes were capped and the contents incubated overnight at room temperature whilst being mixed continuously in a rotating cradle. Two identical series of tubes were mixed in this way.

Subsequent to the incubation period, all tubes were centrifuged for 15 minutes with $2,500 \times g$, whereafter the caps were removed. 0.5 g of powdered tungsten was added to one series of tubes (series A). The tubes were then capped again and the contents mixed by turning the tubes, whereafter the contents were centrifuged for 15 minutes at $2,500 \times g$. The caps were then removed and a further 0.5 g of powdered tungsten added to each tube. The powdered tungsten added last settled gravitationally on the previous sediment. The tubes were then transferred to a measuring instrument of the well-crystal type [$2 \times 2''$ NaI-(TL) crystal with a $20 \times 39$ mm well] with automatic sample changer (LKB - Wallac type 1280 Ultrogamma).

Each tube was measured for a period of 1 minute.

For comparison purposes, subsequent to the first centrifuging step, the second series of tubes (series B) were treated in the following manner in accordance with conventional techniques: The caps were removed. Approximately three quarters of the supernatant (the soluble phase) was removed with suction. This was done by means of a syringe provided with a stop shoulder, thereby enabling the syringe to be inserted to identical depths in all tubes, thereby removing identical amounts of liquid. Subsequent to the removal of this liquid, 2 ml of a 0.9% saline was added to the tubes, the contents of which were then centrifuged. The supernatant was removed by suction as described above. This washing procedure was repeated three times, i.e. practically all radioactivity in the soluble phase was removed in this way. The tube whose contents were prepared for determining the total added radioactivity was not included in the centrifuging and washing procedures. Subsequent to the last withdrawal operation, the residual radioactivity in the tubes was measured, i.e. the activity bound to the solid phase. The measurements were carried out in the same type of apparatus as that described above.

The results are shown in the following table 1.

EXAMPLE 2

This example illustrates the application of the invention in a radioimmuno-assay method of the type double-antibody method (cf. J. Clin. Invest. 41 (1962) pages 254–261).

In a manner corresponding to that disclosed in Example 1, solutions with $^{125}$I-insulin and insulin standard solutions were pipetted to a series of test tubes, although in this case only in duplicates of respective standard concentration. The standard concentrations used were 0; 1.25; 2.5; 5; 10; 20; and 40 μU. To each tube there were then added 300 μl buffer solution containing a specific quantity of antibodies against insulin produced on guinea pigs. 300 μl of buffer solution without antibodies was added to a separate tube. This tube was used for measuring the total amount of radioactivity in each tube. The contents of the tubes were mixed in a so-called Vortex-mixer and incubated thereafter at $+6°$ C. for 18 hours.

In order to precipitate the insulin antibodies, 0.1 ml of antiserum against guinea pig immunoglobulins produced on rabbits and 0.1 ml of guinea pig normal serum, diluted 1:250 with the buffer was added to each tube. The tubes were then incubated overnight. Two identical series were mixed in this way.

0.5 g of tungsten powder was added to one series of tubes (series A), whereafter tubes with their contents were centrifuged for 15 minutes at $2,500 \times g$. The tubes were then transferred to a measuring instrument of the same type as that described in Example 1, where the contents of the tubes were measured for 1 minute.

The second series of tubes (Series B) were treated in accordance with conventional techniques. The tubes were centrifuged directly after the two incubation periods for 15 minutes at $2,500 \times g$. The supernatant containing the soluble radioactivity was then carefully poured from all tubes, except those which had been mixed for measuring the total activity. The precipitate with the residual radioactivity remaining in the tube was then measured in the manner described above. The results are given in the following table 2.

TABLE 2

| Quantity (μU) standard insulin per tube | Percentage radioactivity bound to antibodies | |
|---|---|---|
| | Series A | Series B |
| 0 | 52.1 | 47.8 |
| 0 | 51.0 | 46.8 |
| 1.25 | 43.3 | 41.0 |
| 1.25 | 44.5 | 40.6 |
| 2.5 | 39.4 | 36.0 |

TABLE 1

| | Tubes Series A | | Tubes Series B | | |
|---|---|---|---|---|---|
| Quantity (μU) standard insulin per tube | Impulses per minute | % of total activity | % of total activity absorbed in tungsten powder | Impulses per minute | % of total activity |
| 0 | 8943 | 59.4 | 40.6 | 8369 | 40.3 |
| 0 | 8935 | 59.3 | 40.7 | 8356 | 40.2 |
| 0 | 8667 | 57.6 | 42.4 | 8621 | 41.5 |
| 40 | 11667 | 77.5 | 22.5 | 5049 | 24.1 |
| 40 | 11596 | 77.0 | 23.0 | 5023 | 24.2 |
| 40 | 11475 | 65.2 | 23.8 | 4908 | 23.6 |
| 200 | 13492 | 89.6 | 10.4 | 2059 | 9.9 |
| 200 | 13693 | 90.9 | 9.1 | 2078 | 10.0 |
| 200 | 13587 | 90.2 | 9.8 | 2099 | 10.0 |
| Total activity set for each tube | 15056 | 100 | 100 | 20766 | 100 |

TABLE 2-continued

| Quantity (μU) standard insulin per tube | Percentage radioactivity bound to antibodies | |
|---|---|---|
| | Series A | Series B |
| 2.5 | 39.4 | 36.2 |
| 5 | 30.0 | 27.5 |
| 5 | 29.4 | 27.3 |
| 10 | 21.0 | 22.1 |
| 10 | 21.0 | 20.4 |
| 20 | 14.7 | 14.9 |
| 20 | 15.3 | 14.2 |
| 40 | 7.3 | 10.3 |
| 40 | 10.4 | 10.9 |

The coincidence between the two analyses methods is best seen from the correlation coefficient when $r = 0.998$.

What is claimed is:

1. A method of analysis in which a radioactive substance is distributed in a liquid phase and a solid particle phase and radiation from one phase is measured whilst attenuating the radiation from the other phase, wherein the radiation from said other phase is shielded by virtue of the fact that said phase is mixed with and/or contains a radiation-absorbing material in such a quantity and concentration that the dominant portion of the radiation from this phase will be absorbed.

2. A method as claimed in claim 1, wherein the radiation-absorbing material is in particle form and is insoluble in the liquid phase, and is added to the solid phase prior to or whilst or after separation of said solid phase from the liquid phase.

3. A method as claimed in claim 1, wherein the radiation-absorbing material is in particle form and is insoluble in the liquid phase, and wherein a part of said material is added to the solid phase prior to and/or during separation of said solid phase from the liquid phase, and wherein the residue of said material is added after said separation.

4. A method as claimed in claim 1, wherein the radiation-absorbing material is in particle form of different densities and/or size and wherein said material is insoluble in the liquid phase.

5. A method as claimed in claim 1, wherein the radiation-absorbing material is in a liquid form, not soluble in the liquid phase.

6. A method as claimed in claim 5, wherein more than one liquid radiation-absorbing fluid with different densities are used.

7. A method according to claim 1 in which a combination of liquid and particulate radiation-absorbing material is used.

8. A method as claimed in claim 1, wherein the liquid phase is shielded by using a radiation-absorbing material which is soluble in the liquid phase.

9. A method as claimed in claim 1, wherein the two phases are physically separated by one or more further non-radioactive phases.

10. A method as claimed in claim 1, in which the radiation-absorbing material also adsorbs, binds or otherwise combines with the radioactive material from which the radiation is absorbed.

* * * * *